(12) United States Patent
Tenenbaum

(10) Patent No.: US 8,398,395 B2
(45) Date of Patent: Mar. 19, 2013

(54) ACCESSORY FOR A DENTAL MODEL ARTICULATOR

(75) Inventor: Itzhak Tenenbaum, Holon (IL)

(73) Assignee: Y. T. Dental Solutions Ltd, Azur (IL)

(*) Notice: Subject to any disclaimer, the term of this patent is extended or adjusted under 35 U.S.C. 154(b) by 297 days.

(21) Appl. No.: 12/477,934

(22) Filed: Jun. 4, 2009

(65) Prior Publication Data
US 2009/0305186 A1   Dec. 10, 2009

(30) Foreign Application Priority Data
Jun. 5, 2008   (IL) .......................................... 192008

(51) Int. Cl.
A61C 11/00   (2006.01)

(52) U.S. Cl. ............................................ 433/60; 433/64

(58) Field of Classification Search .............. 433/49–59, 433/60–64, 65–67, 215, 229; 403/56, 76, 403/90, 114, 122
See application file for complete search history.

(56) References Cited

U.S. PATENT DOCUMENTS

| | | | | |
|---|---|---|---|---|
| 1,736,006 A * | 11/1929 | Hagman | ......................... | 433/60 |
| 2,765,533 A * | 10/1956 | McMorris | ....................... | 433/60 |
| 4,196,518 A * | 4/1980 | Benzaria | ........................ | 433/60 |
| 4,200,981 A * | 5/1980 | Fine | ................................ | 433/60 |
| 4,252,523 A * | 2/1981 | Gayso | ............................. | 433/60 |
| 4,460,338 A | 7/1984 | Mercer et al. | | |
| 4,522,591 A | 6/1985 | Braun et al. | | |
| 4,687,442 A * | 8/1987 | Wong | .............................. | 433/63 |
| 4,744,751 A * | 5/1988 | Finkelstein et al. | ........... | 433/60 |
| 5,015,182 A * | 5/1991 | Newberry | ....................... | 433/60 |
| 5,190,455 A * | 3/1993 | Schreiber | ....................... | 433/54 |
| 5,672,055 A * | 9/1997 | Koutavas | ....................... | 433/60 |
| 5,695,333 A * | 12/1997 | Atwood et al. | ................. | 433/57 |
| 5,716,209 A * | 2/1998 | Faierstain | ...................... | 433/60 |
| 5,730,593 A * | 3/1998 | Mack | .............................. | 433/60 |
| 5,749,725 A * | 5/1998 | Chinlund | ....................... | 433/58 |
| 5,795,152 A * | 8/1998 | Glatt | .............................. | 433/60 |
| 6,210,160 B1 * | 4/2001 | Shima | ............................. | 433/60 |
| 7,059,851 B2 * | 6/2006 | Kim | ................................ | 433/60 |
| 7,083,410 B2 * | 8/2006 | Callne | ............................. | 433/58 |
| 7,229,284 B2 * | 6/2007 | Uhm | ............................... | 433/64 |
| 2004/0166468 A1 * | 8/2004 | Hovsepian | ..................... | 433/63 |
| 2008/0206704 A1 * | 8/2008 | Jung | .............................. | 433/60 |

* cited by examiner

Primary Examiner — Cris L Rodriguez
Assistant Examiner — Hao D Mai
(74) Attorney, Agent, or Firm — Deborah Gador

(57) ABSTRACT

An accessory for use with a dental articulator, the accessory including a dental model holder, adapted and configured to hold a dental model, and a mounting assembly for removably affixing said dental model holder to a conventional dental model articulator. In some embodiments, the dental model holder includes a model support, a rear stop member perpendicular to the model support, and a model engaging member mounted in the model support and arranged to engage a dental model and urge it towards the stop member.

13 Claims, 7 Drawing Sheets

ACCESSORY FOR A DENTAL MODEL ARTICULATOR

CROSS-REFERENCE TO RELATED APPLICATIONS

This application claims priority under 35 U.S.C. §119 from Israeli Patent Application No. 192008, filed on Jun. 5, 2008 and entitled "Accessory for a Dental Model Articulator", which is herein incorporated by reference in its entirety.

FIELD OF THE INVENTION

The present invention relates to an accessory for use in production of dental prostheses, in general and, in particular, for use with a dental model articulator.

BACKGROUND OF THE INVENTION

Articulators for producing dental prostheses have long been known. An articulator is a device, which is arranged to hold plaster models of a patient's upper and lower dental arches. The plaster models mounted on the articulator simulate the physiological closure of the two arches for the purpose of manufacturing bridges, prostheses, etc., in a laboratory.

Referring to FIG. 1, there is shown a conventional articulator 10 having lower and upper ring-shaped bases 12, 14 which pivot about an axis 16 relative to one another. An upper model (not shown), replicating the upper dental arch, is fastened by means of a temporary layer of plaster under the lower face of upper base 14, and a lower model (not shown), replicating the lower dental arch, is fastened by means of a similar layer of plaster to the upper face of bottom base 12. Pivoting bases 12 and 14, with the models mounted thereon, relative to each other simulates the movement of the jaw and the dental structure of the mouth.

A disadvantage of using this conventional articulator is that the only way to remove the models from the articulator is by breaking the temporary layer of plaster. This requires special proficiency and very often results in pieces of plaster remaining on the models, and even in breaking the articulator, itself.

In recent years, plasterless articulators were introduced, aiming to avoid the necessity of affixing the models to the articulators with plaster. The plasterless articulators include two integral plates instead of ring-shaped bases: an upper plate and a lower plate, serving as holders for the dental models. Each of the plates includes a securing mechanism configured to engage and lock the model in position. The articulator may include joints enabling the movement of one or both of the plates in different directions relative to one another. However, replacing the simple conventional articulators with these prior art articulators is a significant expense.

Another disadvantage of these prior art articulators is that the plates are substantially the same size as the dental models. Therefore, there is no access to the bottoms of the models, which can be problematic when trying to dislodge a single tooth or group of teeth from a model on the articulator.

Accordingly, there is a long felt need for an inexpensive articulator that does not require affixing of the dental models with plaster, and it would be very desirable if such an articulator were able to utilize existing, conventional articulators.

SUMMARY OF THE INVENTION

There is provided, according to the present invention, an accessory for use with a dental articulator, the accessory including a dental model holder, adapted and configured to hold a dental model, and a mounting assembly for removably affixing the dental model holder to a conventional dental model articulator.

According to one embodiment of the invention, the dental model holder includes a model support, a rear stop member perpendicular to the model support, and a model engaging member mounted in the model support and arranged to engage a dental model and urge it towards the stop member.

According to an alternative embodiment of the invention, the dental model holder includes a model support, a rear stop member perpendicular to the model support, and a model engaging member mounted in the model support and arranged to engage a dental model and urge it towards the stop member, and an articulated arm coupled between the model support and the mounting assembly. According to an alternative embodiment of the invention, the articulated arm includes a rod and at least one ball joint assembly. Ball joint assembly preferably includes a spherical ball member, a socket member having at least one opening for seating the ball member, and a socket locking member for engaging the socket member and locking the ball joint assembly in a desired position.

There is also provided, according to the present invention, a dental articulator having upper and lower bases, the articulator including an upper dental model holder, adapted and configured to hold a dental model, a mounting assembly for removably affixing the upper dental model holder to the upper base, a lower dental model holder, adapted and configured to hold a dental model, and a mounting assembly for removably affixing the lower dental model holder to the lower base.

There is further provided, according to the present invention, a method for forming an accessory for use with a dental model articulator, the method including providing a dental model holder, adapted and configured to hold a dental model, and coupling to the dental model holder a mounting assembly for removably affixing the dental model holder to a conventional dental articulator.

There is also provided, according to the present invention, a method for using a conventional, plaster dental articulator, the method including providing a conventional, plaster dental articulator, and mounting on the articulator at least one accessory including a dental model holder, adapted and configured to hold a dental model, and a plasterless mounting assembly for removably affixing the dental model holder to the conventional dental model articulator.

BRIEF DESCRIPTION OF THE DRAWINGS

The present invention will be further understood and appreciated from the following detailed description taken in conjunction with the drawings in which:

FIG. 6b is a cross section view of the socket member of FIG. 6a;

DETAILED DESCRIPTION OF THE INVENTION

The present invention relates to dental model holders configured to be mounted, as an add-on accessory, on a conventional articulator. The articulator preferably is of the kind used at present to hold dental models with plaster, and the holder includes a plasterless mounting assembly for removably mounting the holder on the articulator. The model holders of the present invention enable use of old fashioned articulators without using plaster, while avoiding the expense of a new, plasterless articulator.

Figure 1:
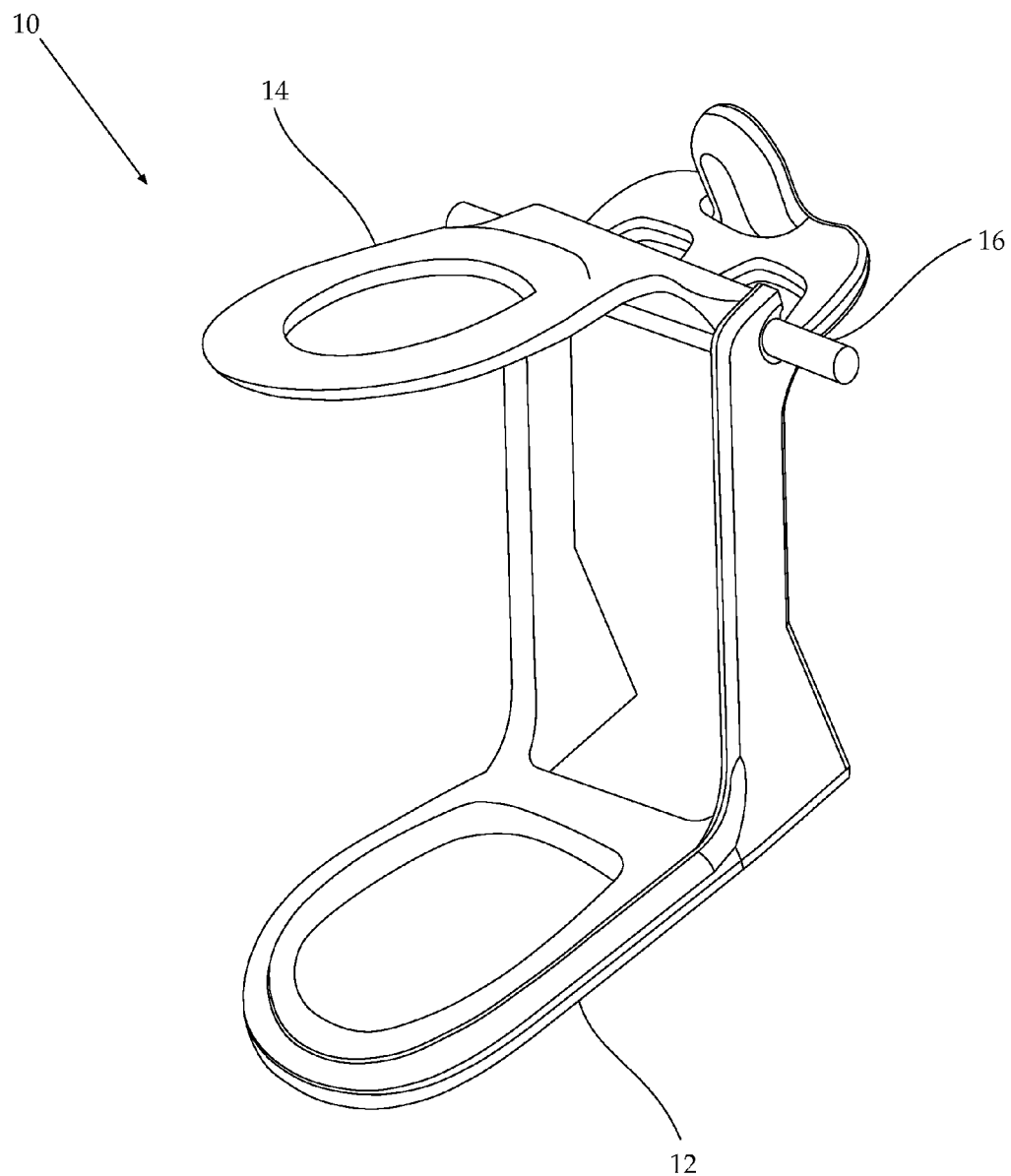
FIG. 1 is a perspective illustration of a prior art articulator.
Figure 2:
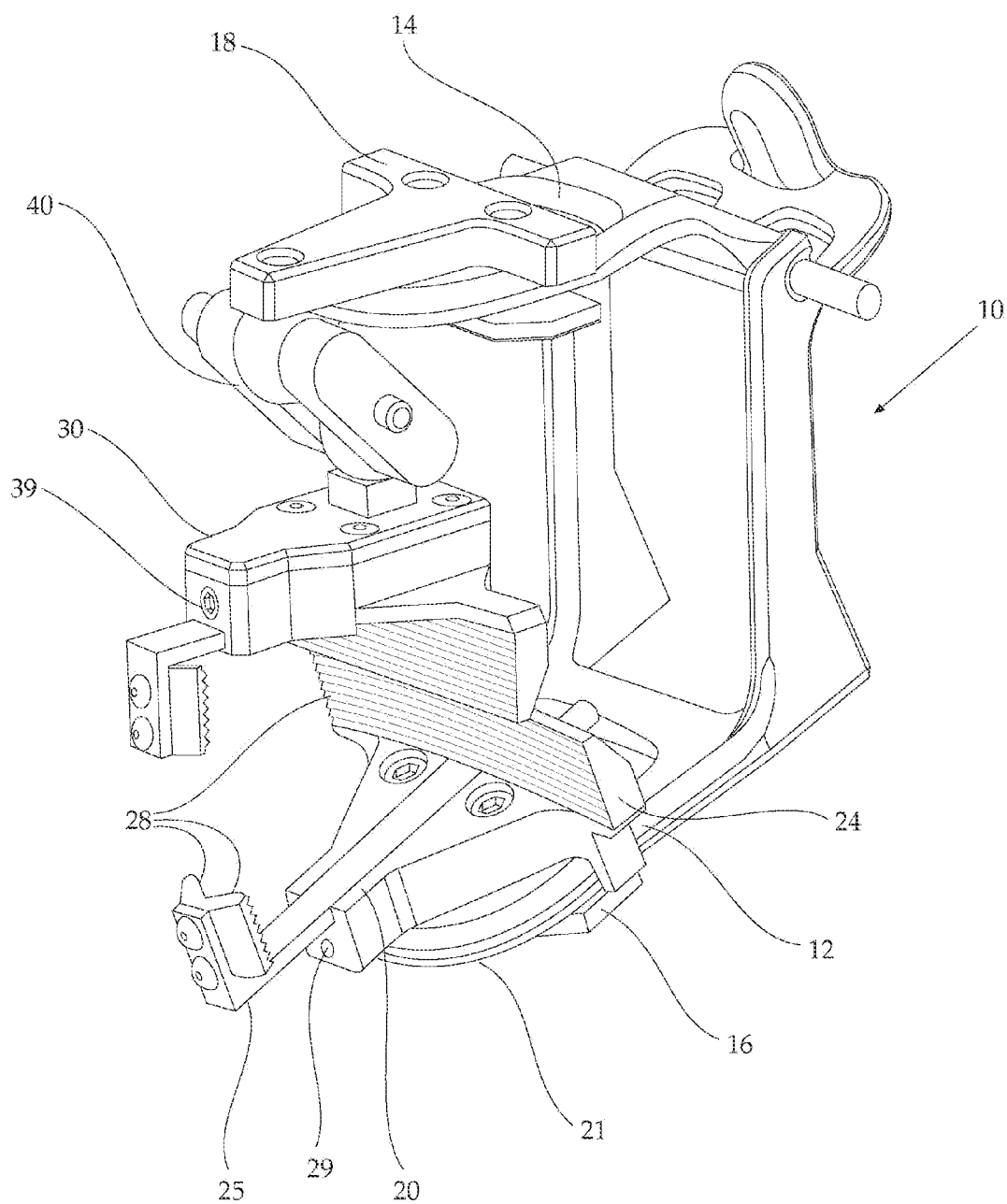
FIG. 2 is a schematic illustration of a prior art articulator with two accessories constructed and operative in accordance with one embodiment of the present invention.

FIG. 2 is a perspective view of a prior art articulator, such as that shown in FIG. 1, with two dental model holders 20, 30 constructed and operative in accordance with one embodiment of the invention. Articulator 10 includes an upper ring-shaped base 14 and a lower ring-shaped base 12. According to this embodiment, a maxillas model holder 30 is mounted on upper base 14 and a mandible model holder 20 is mounted on lower base 12. Mandible model holder 20 is mounted on lower base 12 by means of a mounting assembly 16, which seats in the ring-shaped base and engages portions of the ring. Maxillas model holder 30 includes an articulated arm 40, allowing model holder 30 to swivel in any direction relative to mandible model holder 20. Maxillas model holder 30 further includes a mounting assembly 18 for mounting holder 30 on upper base 14. It is a particular feature of the invention that mounting assemblies 16 and 18 are mechanical elements and do not incorporate plaster.

Figure 3:
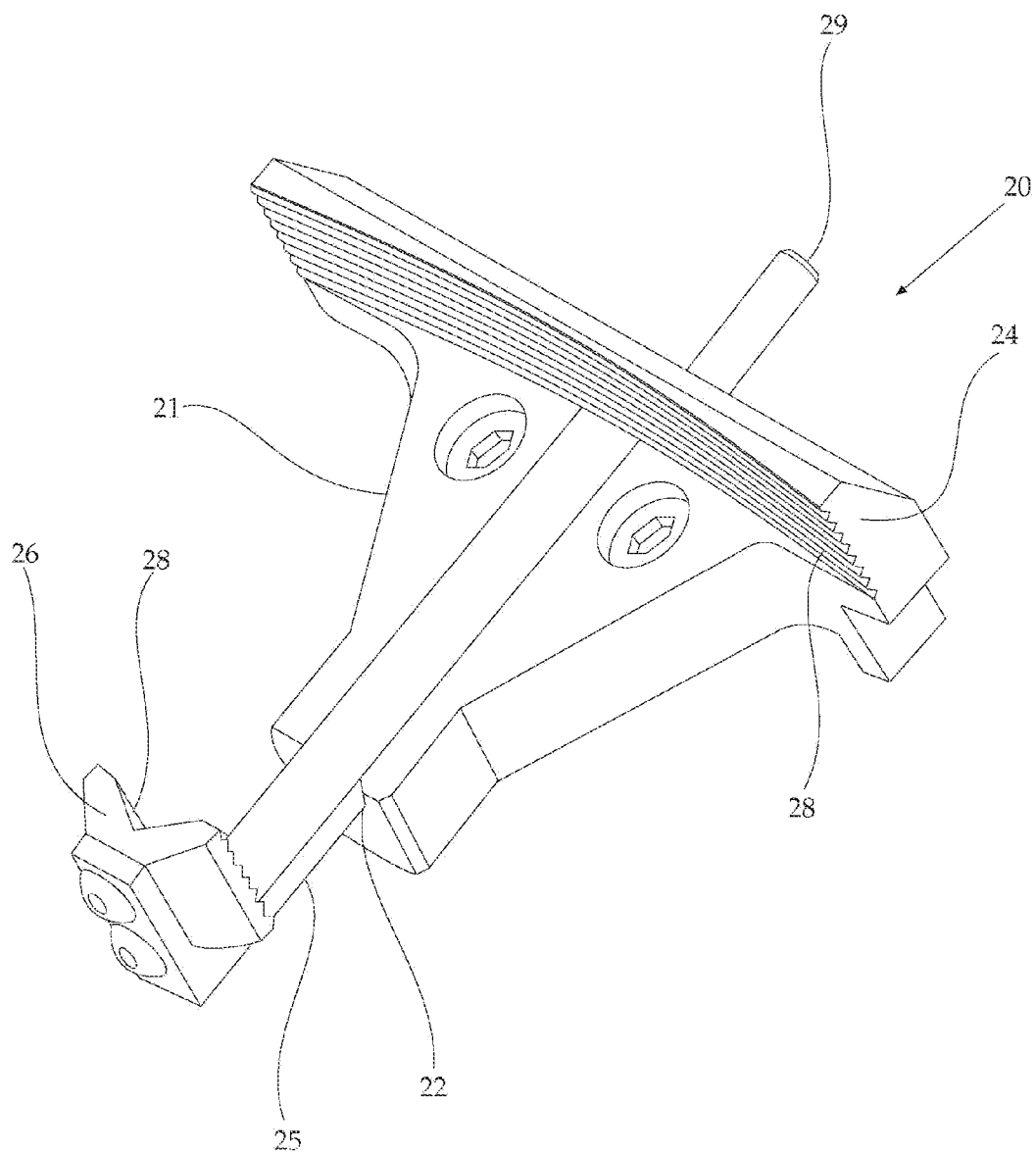
FIG. 3 is a schematic illustration of an accessory, according to one embodiment of the invention, for use with a dental model articulator.

FIG. 3 is a perspective view of the mandible model holder 20 of FIG. 2. Mandible model holder 20 includes a model support 21, a rear stop member 24 perpendicular to support 21, and a securing arm 25. Securing arm 25 includes a model engaging member 26, and is selectably slideable in a track 22 in support 21. Preferably the inner surfaces of stop member 24 and model engaging member 26 include elongated ridges 28, or other similar means to enhance engagement of the dental model, thereby preventing the slipping of the dental model from model holder 20.

Mandible model holder 20 further includes adjustment and locking means for locking securing arm 25 at the desired length, relative to the support 21. According to this embodiment of the invention, the length of securing arm 25 is set by a screw 29, and can be adjusted by turning screw 29 clockwise or counterclockwise. It will be appreciated that, alternatively, any other means may be used to adjust and lock securing arm 25.

According to this embodiment, model engaging member 26 is substantially V-shaped. When the dental model is mounted in holder 20, the front of the dental arch model is engaged by both sides of the V, which thereby applies pressure to both sides of the model, rather than just the front. This special feature also allows for securing a dental model of one half of a dental arch, which at present requires a separate, dedicated articulator.

It is a particular feature of the present invention that support 21 is narrower than the dental model that will be seated thereon. Thus, when a dental model is mounted on support 21, the contour defining the jaw extends beyond support 21 so as to be accessible from the bottom of the articulator, beneath base 12. Thus, the technician always has access to the bottom of the model, in case it is needed for removal of a single tooth or group of teeth from the model for work outside of the model.

Figure 4:
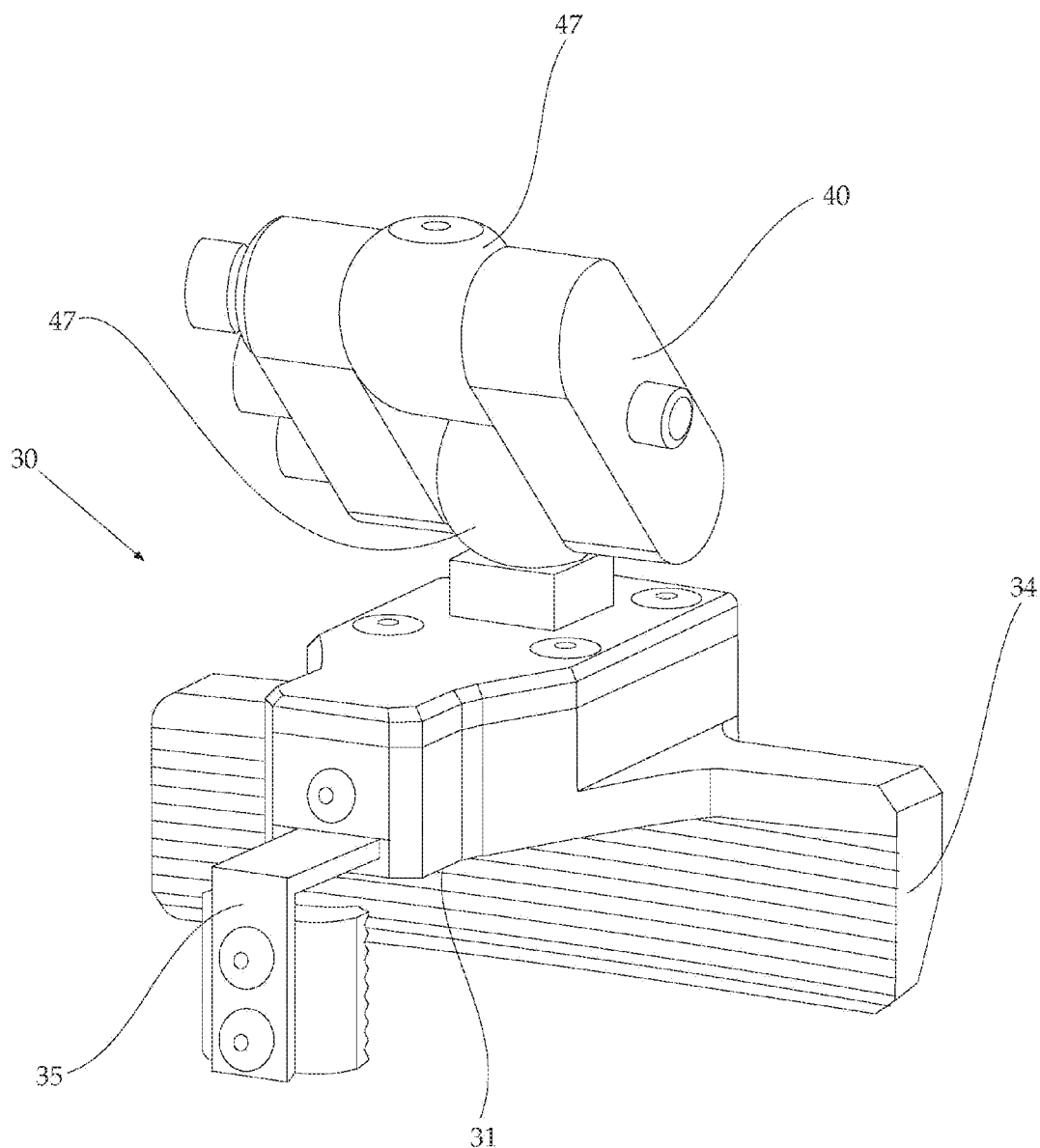
FIG. 4 is a schematic illustration of an accessory, according to another embodiment of the invention, for use with a dental model articulator.
Figure 5:
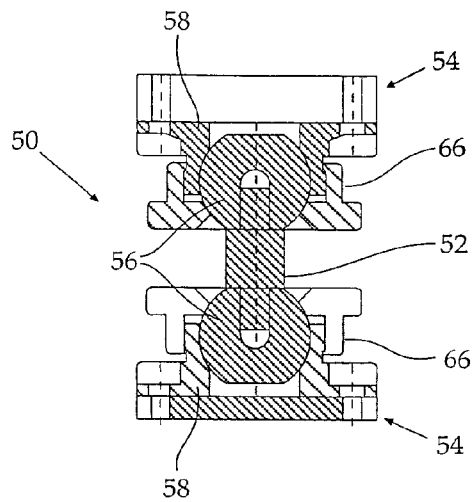
FIG. 5 is a schematic illustration of an articulated arm, according to one embodiment of the invention.

FIG. 4 is a perspective view of the maxillas model holder 30 of FIG. 2. Maxillas model holder 30 is substantially similar to mandible model holder 20, and includes a support 31, a rear stop member 34 perpendicular to support 31, and a securing arm 35. Maxillas model holder 30 further includes an articulated arm 40, allowing model holder 30 to swivel relative to mandible model holder 20. Articulated arm 40 preferably includes two ball joints 47, permitting rotation and swiveling about the joints substantially in all directions. Articulated arm 40 enables movement of maxillas model holder 30 relative to mandible model holder 20 as required to fix the position of the two dental models relative to one another and, thus, to simulate the dental structure of the patient's mouth. According to this embodiment, articulated arm 40 can be extended away from the articulator, thereby facilitating the insertion of the dental models inside model holders 20 and 30.

FIGS. 5 and 6a-6d illustrate an articulated arm 50 according to another embodiment of the invention. Articulated arm 50 includes a rod 52 having a ball joint assembly 54, on each end of the rod. Each ball joint assembly includes a spherical ball member 56 a socket member 58 having two openings 60 and 62 and internal walls, a portion 76 of which is substantially spherical for snugly engaging and receiving a portion of spherical ball member 56, and a socket locking member 66 having internal walls 68, a portion 70 of which is substantially spherical for snugly engaging a portion of spherical ball member 56 and two openings 72 and 74. It will be appreciated that opening 60 of socket member 58 is optional and may not be required in other embodiments of the present invention.

Figure 6A:
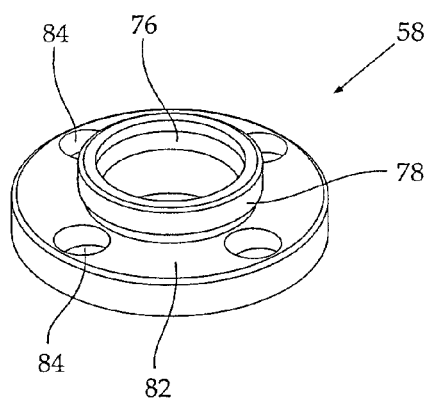
FIG. 6a is a perspective view of a socket member of a ball joint assembly of the articulated arm of FIG. 5, according to one embodiment of the invention.
Figure 6B:
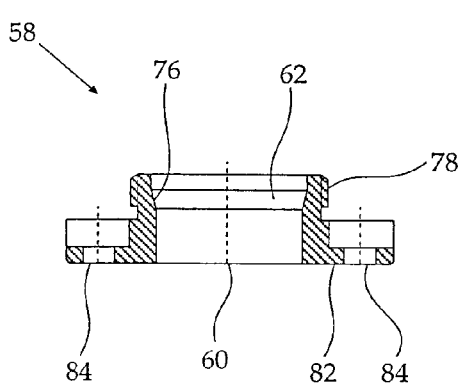

FIG. 6a is a perspective view of socket member 58 and FIG. 6b is a cross section view of the socket member. The internal walls of socket member 58 is partially sloped to form a spherical shaped portion 76 adapted to snugly engage and receive a portion of spherical ball member 56. It will be appreciated that the diameter of sloping spherical shaped portion 76 may be sized according to the diameter of spherical ball member 56. Alternatively, socket member 58 may define an inner concave portion adapted to support spherical ball member 56.

According to one embodiment of the invention, the upper portion of the external walls of socket member 58 adjacent opening 62 define screw threads 78 for coupling the socket member to locking member 66 by screwing screw threads 78 onto matching screw threads 80 defined on the upper portion of the internal walls of locking member 66 adjacent opening 74. Screw threads 78 and matching screw threads 80, permit tightening of locking member 66 to socket member 58 thus locking articulate arm 50 in a desired position. Alternatively, ball member 56 may be locked in socket member 58 by other known means.

According to a preferred embodiment, socket member 58 further includes a base flange 82 having apertures 84 for mounting ball joint 54 on an articulator or a model holder by screws inserted through the apertures.

Figure 6C:
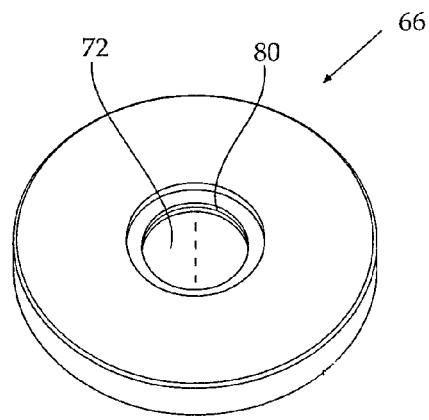
FIG. 6c is a perspective view of a locking member of the socket member of FIGS. 6a and 6b, according to one embodiment of the invention.
Figure 6D:
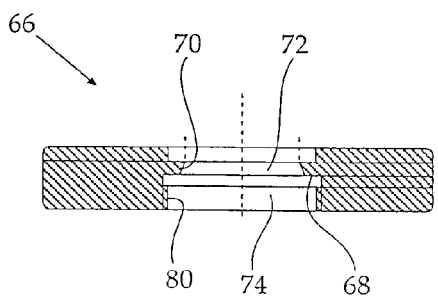
FIG. 6d is a cross section view of the locking member of FIG. 6c.

FIG. 6c is a perspective view of the locking member 66, and FIG. 6d is a cross section view of the locking member of FIG. 6c, according to one embodiment of the invention. As described above, in FIGS. 6c and 6d, there is shown locking member 66 which is substantially cylindrical and having openings 72 and 74. The internal walls 68 include a sloping portion 70 which is substantially spherical for snugly engaging a portion of spherical ball member 56.

Figure 7A:
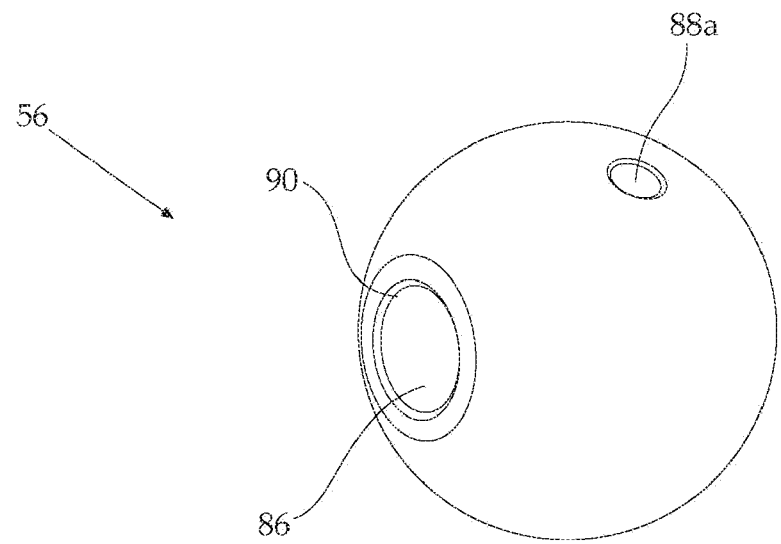
FIG. 7a is a schematic illustration of a ball member of a ball joint assembly of the articulated arm of FIG. 5, according to one embodiment of the invention.
Figure 7B:
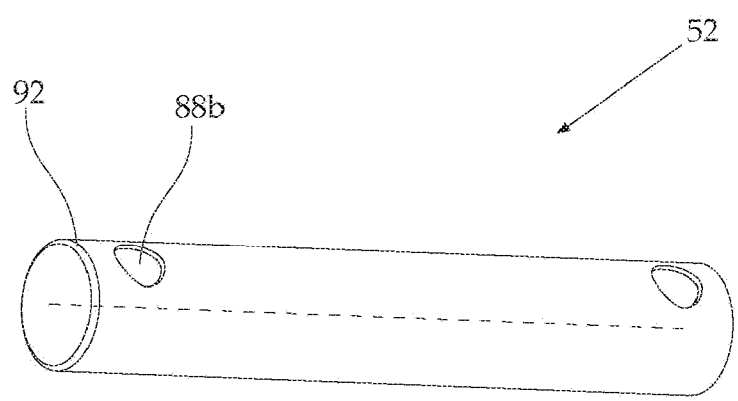
FIG. 7b is a schematic illustration of a rod of the articulated arm of FIG. 5, according to one embodiment of the invention.

FIGS. 7a and 7b are perspective view of ball member 56 and rod 52 according to one embodiment of the invention. Ball member 56 includes a rod bore 86 having an inner diameter substantially the same as the outer diameter of rod 52, allowing for tight insertion of rod 52 into ball member 56. Rod 52 may be fastened to ball member 56 by means of a screw or a fastening pin (not shown), which is inserted through a first fastening aperture 88a in ball 56 and second fastening aperture 88b in rod 52. Alternatively, the internal periphery 90 of rod bore 86 may define screw threads complementary to screw threads 92 defined on the external periphery of rod 52 adjacent each end of the rod. According to another embodiment, ball member 56 and rod 52 may be coupled by other means, such as welding. It will be appreciated that rod 52 may be formed of a plurality of rods coupled to each other in different angles so as to form an articulated arm having freedom of movement and rotation.

Assembling of the ball joints of articulate arm 50 will now be described with further reference to FIGS. 5, 6a-6d and 7a-7b according to one embodiment of the present invention. At first, two locking members 66 are disposed on rod 52 whereby opening 72 of each locking member are adjacent each other and opening 74 of each locking member is facing the end of the rod. Then, one ball member 56 is mounted on each end of rod 52 and secured to the rod in any manner as described above. Thereafter, each ball member is seated in a socket member 58 and a locking member 66 associated with each socket member 58 is shifted along rod 52 in the direction of the socket member until it abuts the ball member, wherein the locking member is tightened to the associated socket member by means of the screw threads described above, for locking each ball joint assembly in the desired position.

Figures 8, 9:
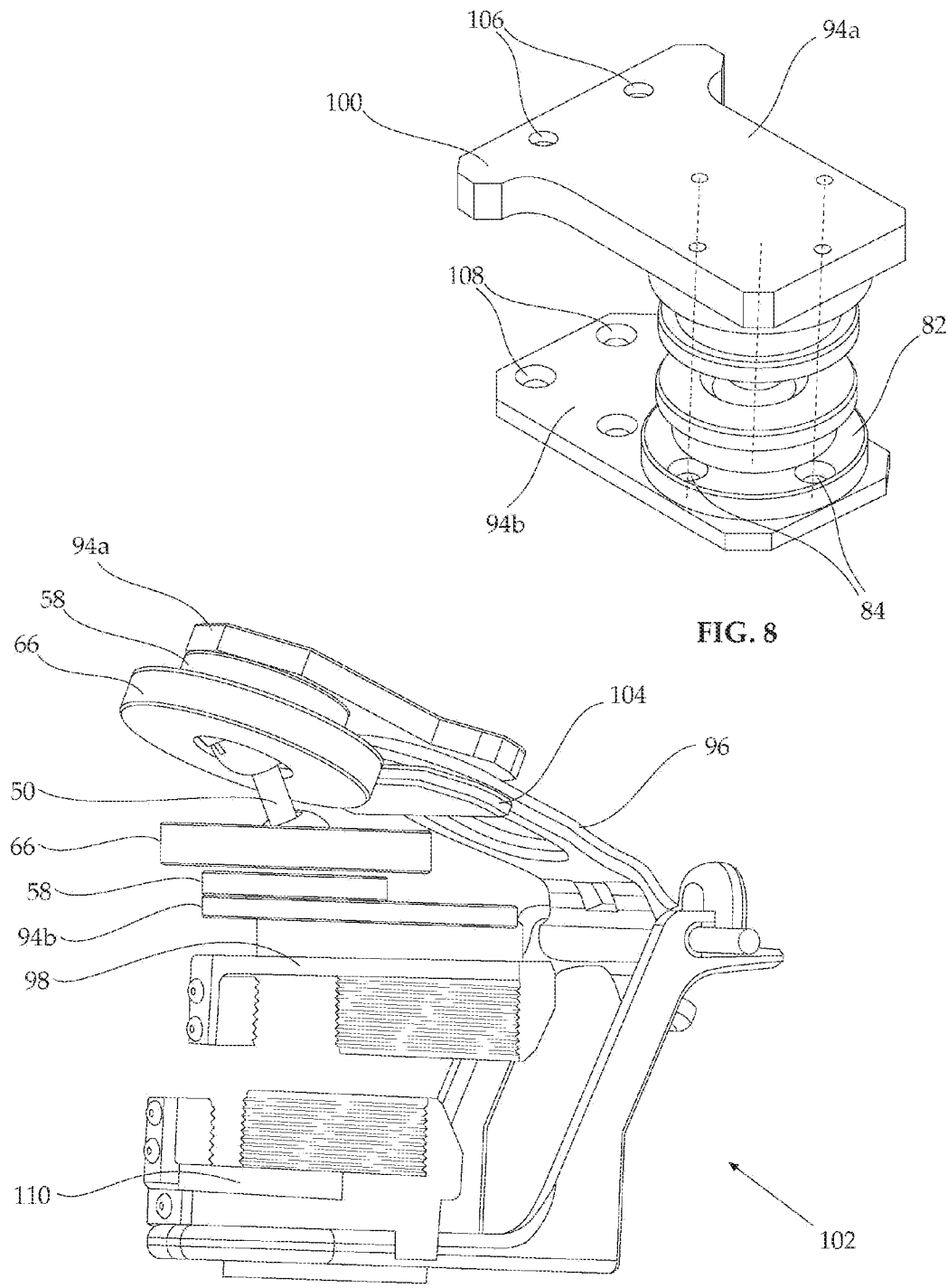
FIG. 8 is a schematic illustration of the articulated arm of FIG. 5 coupled between two mounting members, according to one embodiment of the invention.
FIG. 9 is a schematic illustration of the articulated arm of FIG. 8, mounted on an articulator.

Referring now to FIGS. 8 and 9, there is shown an articulated arm 50 coupled between a first mounting member 94a for mounting arm 50 on an upper base 96, and a second mounting member 94b for mounting a maxillas model holder 98 on arm 50. Arm 50 may be secured to mounting members 94a and 94b by means of screws (not shown). The screws are inserted into holes 84 in base flange 82 of each socket member and screwed into the adjacent mounting members. Mounting member 94a includes shoulders 100 for coupling arm 50 to upper base 96 of an articulator 102 as can be seen in FIG. 9. Mounting member 94a may be secured to upper base 96 by a clamping member 104 and screws (not shown) which may be inserted into clamping holes 106 and screwed into clamping member 104. Maxillas model holder 98 may be secured to arm 50 by screws (not shown) which may be inserted into securing holes 108 in mounting member 94b and screwed into maxillas model holder 98. It will be appreciated that mounting one end of arm 50 on base 96 and mounting Maxillas model holder 98 on the second end of arm 50 may be accomplished in various conventional ways, as known.

Articulated arm 50 permits moving maxillas model holder 98 relative to mandible model holder 110 for fixing the position of the two dental models relative to one another as required for simulating the dental structure of the patient's mouth. It will be appreciated that according to an alternative embodiment of the present invention, articulated arm 50 may include a single ball joint 54, however in this arrangement the positioning of maxillas model holder 98 relative to mandible model holder 110 will be limited.

Operation of the articulator of FIG. 2 will now be described, with further reference to FIGS. 2 to 4. A maxillas model holder 30 is mounted on the upper ring 14 of a conventional articulator and removably fastened in place by means of mounting assembly 18. A mandible model holder 20 is mounted on the lower ring 12 of the articulator and removably fastened by means of mounting assembly 16. Articulated arm 40 is extended away from mandible model holder 20 to permit placement of a dental model (not shown) on support 21 adjacent rear stop member 24. After placing the dental model on support 21, securing arm 25 is retracted in holder 20 until it engages the front of the dental model and urges the dental model towards stop member 24. Thus, the mandible dental model is secured between model engaging member 26 and rear stop member 24, inside holder 20.

In a similar fashion to the mandible model, the maxillas model is affixed to the holder 30. After securing the upper dental model in holder 30, articulated arm 40 is manipulated, positioning maxillas model holder 30 in the position relative to mandible model holder 20 simulating the patient's jaw. It will appreciated that the flexibility of the maxillas model holder permits the technician to position the maxillas model facing the mandible model for a good match and to simulate the patient's bite.

The model holders of the present invention permit a technician to provide clean and aesthetic dental arch models and permit easy mounting and removal of dental models on the articulator. Furthermore, the model holders can be moved from articulator to articulator, as required. An additional advantage of the present device is that a single model holder can hold securely a full or half jaw, as desired.

According to alternative embodiments of the invention, the upper and lower holders can be the same—both can be the holder of FIG. 3, or both can be the holder of FIG. 4 having an articulated arm. According to further embodiments, different types of joints, other than an articulated arm, can be utilized in one or both of the holders.

It will be appreciated that, while the articulator has been described with the mandible model holder affixed to the bottom base of the articulator and the maxillas model holder freely rotatable on the articulated arm affixed to the upper base of the articulator, the invention can also be utilized with the models mounted on the opposite bases of the articulator. It will further be appreciated that model holders 20, 30 can be mounted on other types of conventional articulators than that shown in FIG. 1.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

The invention claimed is:

1. An accessory for use with a dental articulator, the accessory comprising:
   a dental model holder, adapted and configured to hold a dental model; and
   a mounting assembly for removably affixing said dental model holder to a dental model articulator designed and configured for holding dental models by means of a temporary layer of plaster;
   said mounting assembly including:

a removable mounting member; and
an articulated arm coupled between said dental model holder and said mounting member, said articulated arm including:
a rod; and
two independently manipulable and lockable ball joint assemblies, one coupled to each end of the rod, one of said ball joint assemblies being coupled to the dental model holder, and another one of said ball joint assemblies being coupled to said mounting member, permitting rotation and swiveling of the dental model holder about the ball joint assemblies substantially in all directions;
each of said ball joint assemblies further including:
a spherical ball member;
a socket member having at least one opening and substantially spherical internal walls for snugly engaging and receiving a portion of said spherical ball member; and
a socket locking member having internal walls, a portion of said walls being substantially spherical for snugly engaging a portion of said spherical ball member, and screw threads about an opening on said socket locking member cooperating with screw threads about said at least one opening of said socket member to tighten said socket locking member to said socket member about said spherical ball member, for independently locking said ball joint assembly in a desired position with said spherical ball member locked against rotation by and between the spherical internal walls of the socket member and the spherical portion of the internal walls of the socket locking member.

2. The accessory according to claim 1, wherein said dental model holder includes:
a model support;
a rear stop member perpendicular to said model support; and
a model engaging member mounted in said model support and arranged to engage a dental model and urge it towards said stop member.

3. The accessory according to claim 2, wherein said model engaging member is V-shaped and includes an adjustable securing arm.

4. The accessory according to claim 1, wherein
said removable mounting member is adapted and configured for mounting said articulated arm on said dental articulator; and
further comprising a second mounting member for mounting said model holder on said articulated arm.

5. The accessory according to claim 1, wherein said mounting assembly is a plasterless mounting assembly for use with a dental articulator designed and configured for holding dental models by means of a temporary layer of plaster.

6. A dental articulator comprising:
a dental articulator having an upper base and a lower base, designed and configured for holding dental models by means of a temporary layer of plaster;
an upper dental model holder, adapted and configured to hold a dental model;
a plasterless mounting assembly for removably affixing said upper dental model holder to said upper base;
a lower dental model holder, adapted and configured to hold a dental model; and
a plasterless mounting assembly for removably affixing said lower dental model holder to said lower base;
said mounting assembly for said upper dental model holder including a removable mounting member and an articulated arm coupled between said dental model holder and said mounting member, said articulated arm including:
a rod; and
two independently manipulable and lockable ball joint assemblies, one coupled to each end of said rod, one of said ball joint assemblies being coupled to the dental model holder, and another one of said ball joint assemblies being coupled to said mounting member, permitting rotation and swiveling of the dental model holder about the ball joint assemblies substantially in all directions;
each of said ball joint assemblies further including:
a spherical ball member;
a socket member having at least one opening and substantially spherical internal walls for snugly engaging and receiving a portion of said spherical ball member; and
a socket locking member having internal walls, a portion of said walls being substantially spherical for snugly engaging a portion of said spherical ball member, and screw threads about an opening on said socket locking member cooperating with screw threads about said at least one opening of said socket member to tighten said socket locking member to said socket member about said spherical ball member, for independently locking said ball joint assembly in a desired position with said spherical ball member locked against rotation by and between the spherical internal walls of the socket member and the spherical portion of the internal walls of the socket locking member.

7. The articulator according to claim 6, wherein said lower dental model holder is narrower than a dental model to be seated thereon.

8. The articulator according to claim 6, wherein at least one of said dental model holders includes:
a model support;
a rear stop member perpendicular to said model support; and
a model engaging member mounted in said model support and arranged to engage a dental model and urge it towards said stop member.

9. The articulator according to claim 8, wherein said model engaging member is V-shaped and includes an adjustable securing arm.

10. The articulator according to claim 6, further comprising:
a second model support;
said second model support being narrower than a dental model seated thereon, whereby a contour of said model defining the jaw extends beyond said support so as to be accessible from beneath said articulator.

11. A method for forming an accessory for use with a dental model articulator, the method comprising:
providing a dental model holder, adapted and configured to hold a dental model in the absence of plaster; and
coupling said dental model holder to a first end of a rod by a first ball joint assembly;
coupling a second end of said rod to a second ball joint assembly coupled to a mounting member, said second ball joint assembly being manipulable and lockable independently of said first ball joint;
said steps of coupling including:
mounting one spherical ball member on each end of said rod and securing said ball member to said rod;

seating each ball member in a socket member;

shifting a locking member associated with each socket member along said rod in the direction of the socket member until it abuts the ball member; and independently tightening each said locking member to the socket member of the same ball joint assembly by means of complementary screw threads, thereby locking each ball joint assembly in the desired position with said spherical ball member releasably locked against rotation by said socket member and said socket locking member; and removably affixing said mounting member to a dental articulator.

12. The method according to claim 11, further comprising:

providing a dental articulator having an upper and a lower base, designed and configured for holding dental models by means of a temporary layer of plaster;

wherein said step of providing a dental model holder includes constructing an upper dental model holder for holding an upper dental model;

and said step of coupling includes removably affixing said upper dental model holder to said upper base by said mounting assembly in the absence of plaster;

constructing a lower dental model holder for holding a lower dental model; and removably affixing said lower dental model holder to said lower base by a lower plasterless mounting assembly.

13. The method according to claim 12, wherein said step of constructing a lower dental model holder includes constructing a lower dental model holder that is narrower than a lower dental model, whereby a contour of said lower dental model defining the jaw extends beyond said lower dental model holder so as to be accessible from beneath said articulator.

* * * * *